ize="7">United States Patent [19]

Burow, Jr. et al.

[11] Patent Number: 4,643,758

[45] Date of Patent: Feb. 17, 1987

[54] HERBICIDAL FURYL-, THIENYL- AND PYRROLYL-2-PYRROLIDINONES

[75] Inventors: Kenneth W. Burow, Jr.; James C. Williams, Jr., both of Indianapolis, Ind.

[73] Assignee: Eli Lilly and Company, Indianapolis, Ind.

[21] Appl. No.: 669,396

[22] Filed: Nov. 8, 1984

Related U.S. Application Data

[62] Division of Ser. No. 431,877, Sep. 30, 1982, abandoned.

[51] Int. Cl.$^4$ ............ C07D 403/04; C07D 405/04; C07D 409/04; A01N 43/10
[52] U.S. Cl. ............................................ 71/90; 71/95; 548/517; 548/518; 548/527; 548/531; 548/537; 548/538; 549/61; 549/69; 549/474; 549/480
[58] Field of Search ............ 548/518, 517, 527; 71/90, 95

[56] References Cited

U.S. PATENT DOCUMENTS

| | | | |
|---|---|---|---|
| 3,040,004 | 6/1962 | Glickman et al. | 548/518 |
| 3,823,161 | 7/1974 | Lesser | 260/332.2 |
| 4,013,681 | 3/1977 | Karabinos et al. | 260/332.2 |
| 4,075,001 | 2/1984 | Gibbons | 71/90 |
| 4,088,773 | 5/1978 | Evans et al. | 424/274 |
| 4,178,167 | 12/1979 | Schneider et al. | 548/550 X |
| 4,178,168 | 12/1979 | Schneider et al. | 71/95 |
| 4,195,181 | 3/1980 | Metzger et al. | 71/90 X |
| 4,240,820 | 12/1980 | Dickore' et al. | 71/76 |
| 4,318,858 | 3/1982 | Hirai et al. | 548/517 X |
| 4,337,081 | 6/1982 | Gay | 71/90 |
| 4,416,683 | 11/1983 | Burow, Jr. | 71/90 |
| 4,452,989 | 6/1984 | Deckner et al. | 548/537 |
| 4,500,343 | 2/1985 | Burow, Jr. | 71/88 X |

FOREIGN PATENT DOCUMENTS

| | | |
|---|---|---|
| 2828265 | 6/1978 | Fed. Rep. of Germany . |
| 3020575 | 12/1981 | Fed. Rep. of Germany . |
| 49-016861 | 4/1974 | Japan . |
| 1226913 | 3/1971 | United Kingdom . |

OTHER PUBLICATIONS

Derwent Abstract, 05558c.
Sowell, Sr. et al., "New Synthesis . . . Activity", J. Pharm. Sci., 65(6), 908–10, (1976).
Derwent Abstract, 3919v.
Derwent Abstract, 93226d.

*Primary Examiner*—Donald G. Daus
*Assistant Examiner*—William A. Teoli, Jr.
*Attorney, Agent, or Firm*—Joseph A. Jones

[57] ABSTRACT

N-(Substituted heterocyclic)-2-pyrrolidinone derivatives useful as herbicides both alone and in combination with other herbicides.

20 Claims, No Drawings

HERBICIDAL FURYL-, THIENYL- AND PYRROLYL-2-PYRROLIDINONES

This application is a division of application Ser. No. 431,877, filed Sept. 30, 1982 now abandoned.

SUMMARY OF THE INVENTION

The present invention relates to a compound of the formula

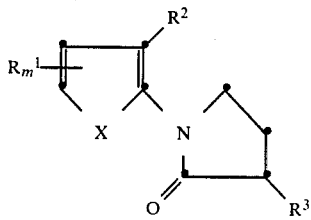

wherein:
$R^1$ is $C_1$–$C_{10}$ alkyl or $C_3$–$C_8$ cycloalkyl;
$R^2$ is cyano or

$R^3$ is $C_1$–$C_6$ alkyl;
$R^4$ is hydroxy, $C_1$–$C_6$ alkoxy or $NH_2$;
m is 1 or 2; and
X is O, S or NH.

The present invention also provides a herbicidal method for the use of the compounds, as well as compositions containing such compounds. Combinations of a present compound with one or more herbicides are also provided herein.

Also provided by the present invention are intermediates of the formula

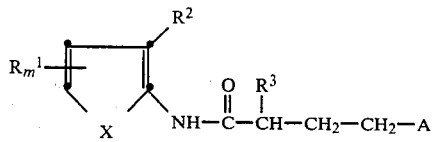

wherein:
$R^1$ is $C_1$–$C_{10}$ alkyl or $C_3$–$C_8$ cycloalkyl;
$R^2$ is cyano or

$R^3$ is $C_1$–$C_6$ alkyl;
$R_4$ is hydroxy, $C_1$–$C_6$ alkoxy or $NH_2$;
m is 1 or 2;
X is O, S or NH; and
A is halogen.

DETAILED DESCRIPTION OF THE INVENTION

In the above formula, $C_1$–$C_{10}$ alkyl includes methyl, ethyl, n-propyl, isopropyl, n-butyl, sec.-butyl, isobutyl, t-butyl, n-pentyl, isopentyl, sec.-pentyl, neopentyl, n-hexyl, sec.-hexyl, isohexyl, n-heptyl, isoheptyl, sec.-heptyl, n-octyl, sec.-octyl, isooctyl, n-nonyl, sec.-nonyl, isononyl, n-decyl, sec.-decyl, and the like.

$C_3$–$C_8$ Cycloalkyl represents saturated monocyclic cycloalkyl groups such as cyclopropyl, cyclobutyl, cyclopentyl, cyclohexyl, cycloheptyl, and cyclooctyl.

The term "halogen", as defined herein, represents fluorine, chlorine, bromine and iodine. Chlorine and bromine are preferred.

The compounds listed below are typical of the compounds provided by the present invention. It will be understood that the compounds specifically named herein do not bound the scope of the invention, but are presented merely to assure that agricultural chemists will fully understand this invention.

N-(3-Carboxy-4-ethyl-2-furyl)-3-methyl-2-pyrrolidinone

N-[3-Cyano-4-(1,1-dimethylethyl)-2-furyl]-3-propyl-2-pyrrolidinone

N-[3-Carbmethoxy-4-(1-methylethyl)-5-(1-methylethyl)-2-thienyl]-3-methyl-2-pyrrolidinone N-[3-Cyano-4-(cyclopropyl)-2-pyrrolyl]-3-methyl-2-pyrrolidinone N-[3-Carboxamide-4-(1-methylethyl)-2-thienyl]-3-methyl-2-pyrrolidinone N-[3-Cyano-4-cyclohexyl-2-furyl]-3-methyl-2-pyrrolidinone N-[3-Cyano-4-(1-methylethyl)-5-methyl-2-pyrrolyl]-3-methyl-2-pyrrolidinone N-[3-Cyano-4-(1,1-dimethylethyl)-2-furyl]-3-ethyl-2-pyrrolidinone N-(3-Cyano-4-cyclohexyl-2-thienyl)-3-methyl-2-pyrrolidinone N-[3-Carbethoxy-4-(1,1-dimethylethyl)-2-pyrrolyl]-3-methyl-2-pyrrolidinone Preferred compounds and intermediates have the above formula wherein $R^3$ is methyl, m is one, $R^1$ exists at the 4-position and $R^2$ is cyano. Especially preferred compounds have the above formula and $R^1$ is $C_4$–$C_{10}$ alkyl.

The compounds of the present invention may be prepared by procedures well known to those skilled in the art. The preferred process involves reacting a 2-amino heterocycle derivative with a halogen derivative to provide the corresponding 4-halo-N-(substituted heterocycle)-2-alkylbutanamide intermediate, which is then cyclized in base to provide a pyrrolidinone of the invention. The scheme for this reaction is as follows:

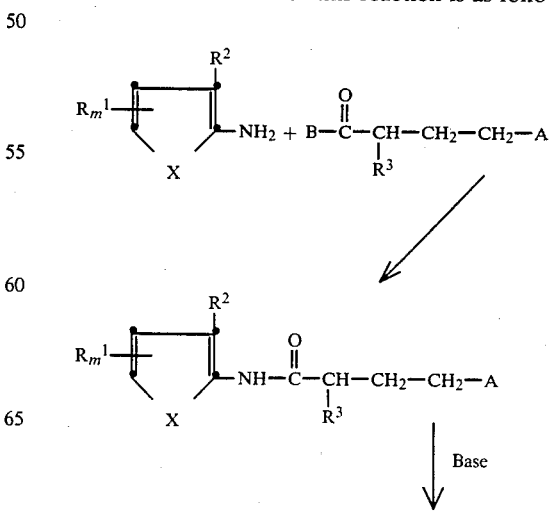

-continued

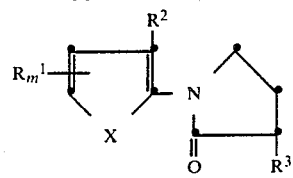

wherein $R^1$, $R^2$, $R^3$, m, X and A are as defined above and B is a good leaving group such as halogen, $C_1$–$C_6$ alkoxy,

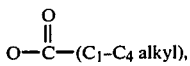

and the like.

The first step of this reaction procedure involves the preparation of an intermediate of the invention and is typically performed in a hydrocarbon solvent such as benzene, toluene, xylenes, hexanes, octane and the like. Of these, benzene is the solvent of choice. The reaction temperature may be from about 30° C. to about 200° C., more preferably at the reflux temperature of the reaction mixture. When the product has formed, which usually takes from about 1 hour to about 10 days, the reaction is worked up according to standard procedures. Typically, the solvent is evaporated under reduced pressure. The intermediate thus formed may then be further purified by either column chromatography or crystallization according to standard procedures.

The second step of the above described reaction may simply involve washing a water immiscible solution containing the intermediate of the invention formed in the first step with a suitable base. Examples of such water immiscible solvents include benzene, toluene, diethyl ether, ethyl acetate, dichloromethane and the like. Suitable bases include aqueous sodium hydroxide or potassium hydroxide. The water immiscible solvent may then be washed with dilute acid or water and evaporated under vacuum. The pyrrolidinone thus formed may be purified if desired by any of several procedures well known to those skilled in the art.

It may be necessary to employ a stronger base than the one used in the above described washing procedure to provide a compound of the invention. Examples of stronger bases which may be employed are sodium alkoxide derivatives such as sodium methoxide or ethoxide. Typically this reaction is conducted in an alcohol, such as methanol or ethanol, at a temperature of from about 20° C. to 150° C. Typically the solvent is removed once the product has formed. The residue is then typically dissolved in a water immiscible solvent, such as ethyl acetate, and washed with water. The solvent is then normally evaporated and the product purified if desired.

The starting materials used to prepare compounds and intermediates of the invention are either commercially available or readily prepared by known procedures. For example, 2-aminothiophene derivatives are prepared by reacting a malonic acid nitrile derivative with an appropriate ketone analog in the presence of ammonium acetate and acetic acid to provide an alkene derivative, which is finally reacted with sulfur in the presence of morpholine to provide the corresponding 2-aminothiophene derivative. The scheme for this reaction is as follows:

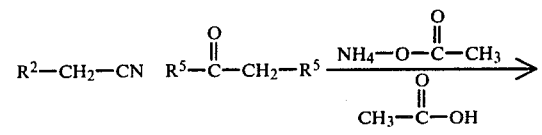

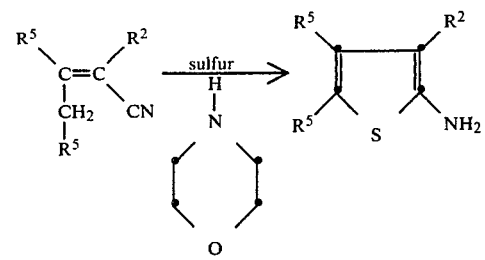

wherein $R^2$ is as defined above, and $R^5$ is hydrogen, $C_1$–$C_{10}$ alkyl or $C_3$–$C_8$ cycloalkyl, provided that no more than one $R^5$ is hydrogen.

The compounds of the present invention may also be conveniently prepared by reacting a lactam salt with a heterocycle according to the following scheme:

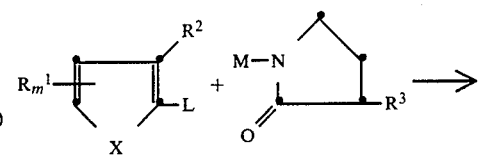

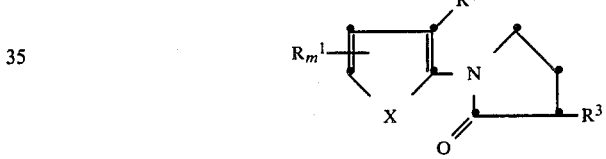

wherein $R^1$, $R^2$, $R^3$ and m are as defined above, M is a group IA or IIA metal and L is a leaving group.

This reaction is carried out under anhydrous conditions using any suitable inert solvent. The ethers such as diethyl ether, dioxane and tetrahydrofuran are particularly useful; however, solvents such as dimethylformamide (DMF), N-methylpyrrolidone and hexamethylphosphoric triamide may also be employed. The reaction is typically carried out at temperatures between 0° and 110° C., preferably between 0° and 40° C., most preferably at room temperature. The product has usually formed after about 1 to 6 hours. The product thus formed is then isolated and purified by procedures well known to those skilled in the art.

In the above reaction scheme a preferred lactam salt is a lithium derivative. Preferred leaving groups on the hetercyclic ring include halogen, more preferably chlorine, bromine and iodine.

In addition to the synthetic procedures described above, certain compounds and intermediates of the present invention may be prepared by modification of an existing compound or intermediate of the invention, respectively. For example, aromatic heterocyclic derivatives of the invention having a carboxamide moiety at the 3-position may be conveniently prepared by simply reacting the corresponding cyano derivative with a suitable oxidizing agent, such as hydrogen peroxide, according to known procedures.

The following detailed examples are provided in an effort to more fully illustrate specific aspects of the present invention. The examples are not intended to be limiting in any respect and should not be so construed.

EXAMPLE 1

N-[3-Cyano-4-(1,1-dimethylethyl)-2-furyl]-3-methyl-2-pyrrolidinone

A. 1-Bromo-3,3-dimethyl-2-butanone

A solution of 30.0 g of 3,3-dimethyl-2-butanone dissolved in 150 ml of diethyl ether was cooled to about 0°–5° C. with an ice bath. To the solution was added 25.0 g of bromine dropwise and the reaction mixture was allowed to warm to about 20° C. The mixture was washed with water and the organic phase was separated, dried over anhydrous magnesium sulfate and filtered. The solution was concentrated under vacuum to afford 25.0 g of 1-bromo-3,3-dimethyl-2-butanone as an oil. Yield 47%.

B. 3,3-Dimethyl-2-butanon-1-ol

To a solution of 27.7 g of potassium formate dissolved in 200 ml of methanol was added 40.0 g of 1-bromo-3,3-dimethyl-2-butanone. The reaction mixture was refluxed overnight and the methanol was distilled off. The precipitated salt was collected by filtration and washed with anhydrous diethyl ether. The filtrate was distilled under reduced pressure to afford 17.0 g of 3,3-dimethyl-2-butanon-1-ol. Yield 67%.

C. 2-Amino-3-cyano-4-(1,1-dimethylethyl)furan

To a solution of 17.0 g of 3,3-dimethyl-2-butanon-1-ol and 9.6 g of malononitrile dissolved in 100 ml DMF was added 12.71 g of morpholine at room temperature. The mixture was stirred at this temperature overnight and the volatiles were removed in vacuo. The resulting residue was added to ice water and stirred for 30 minutes. The precipitate was collected by filtration, redissolved in a small amount of DMF and slurried in ice water again. The precipitated solid was again collected by filtration and dried to afford 14.3 g of 2-amino-3-cyano-4-(1,1-dimethylethyl)furan. mp=83°–85° C. Yield 61%.

D. To 4.0 g of 2-amino-3-cyano-4-(1,1-dimethylethyl)furan and 4.3 g of 2-methyl-4-chlorobutyryl chloride was added 150 ml of toluene. The reaction mixture was allowed to reflux for about 72 hours. The mixture was washed once with 1N hydrochloric acid, once with 2N sodium hydroxide and finally with water. The organic phase was dried over anhydrous magnesium sulfate, filtered and concentrated under vacuum. The residue was chromatographed over silica gel while eluting with an 80/20 mixture of Skellysolve B/ethyl acetate. Fractions containing the major component were combined and the solvent was evaporated therefrom to afford 1.3 g of N-[3-cyano-4-(1,1-dimethylethyl)-2-furyl]-3-methyl-2-pyrrolidinone. mp=88°–90° C. Yield 21%.

EXAMPLE 2

N-[3-Cyano-4-(1,1-dimethylethyl)-2-thienyl]-3-methyl-2-pyrrolidinone

A. 2-(1,1-Dimethylethyl)-1,1-dicyano-1-propene

A solution of 9.9 g of malononitrile, 26.25 g of 3,3-dimethyl-2-butanone, 1.45 g of ammonium acetate and 2.25 g of acetic acid dissolved in 100 ml of toluene was refluxed for about 16 hours with the aid of a Dean-Stark Trap. The reaction mixture was diluted with 120 ml of toluene and washed with 200 ml water. The organic phase was collected, dried over anhydrous magnesium sulfate, filtered and concentrated under vacuum. The resulting residue was distilled under vacuum to afford 15.2 g of 2-(1,1-dimethylethyl)-1,1-dicyano-1-propene as an oil. Yield 68%.

B. 2-Amino-3-cyano-4-(1,1-dimethylethyl)thiophene

To a solution of 15.2 g of 2-(1,1-dimethylethyl)-1,1-dicyano-1-propene and 3.2 g of sulphur dissolved in 80 ml ethanol was added 8.9 g of morpholine dropwise at 45°–50° C. The mixture was stirred for an additional 1½ hours while maintaining the 50° C. temperature and the volatiles were removed in vacuo. The residue was added to ice water and the precipitated solid was collected by filtration, washed with water and dried to afford about 12.0 g of 2-amino-3-cyano-4-(1,1-dimethylethyl)thiophene. Yield 65%.

C. 4-Chloro-N-[3-cyano-4-(1,1-dimethylethyl)-2-thienyl]-2-methylbutanamide

A mixture of 4.0 g of 2-amino-3-cyano-4-(1,1-dimethylethyl)thiophene and 4.0 g of 2-methyl-4-chlorobutyryl chloride dissolved with 100 ml benzene was refluxed for about 72 hours. The solvent was evaporated under reduced pressure and the residue was chromatographed while eluting with a 90/10 mixture of Skellysolve B/ethyl acetate. Fractions containing the major component were combined and the solvent was evaporated therefrom to afford 3.75 g of 4-chloro-N-[3-cyano-4-(1,1-dimethylethyl)-2-thienyl]-2-methylbutanamide. mp=115°–116° C. Yield 57%.

Analysis calculated for $C_{14}H_{19}ClN_2OS$: Theory: C, 56.27; H, 6.41; N, 9.37; Found: C, 56.37; H, 6.28; N, 9.09.

D. To a solution of 0.21 g of sodium dissolved in 10 ml of ethanol was added 2.75 g of 4-chloro-N-[3-cyano-4-(1,1-dimethylethyl)-2-thienyl]-2-methylbutanamide dissolved in 35 ml ethanol dropwise. The mixture was allowed to stir at room temperature for about one hour and the solvent was removed in vacuo. The residue was combined with 10 ml ethanol and 250 ml water and the precipitate was collected by filtration. The collected solid was recrystallized from hexane to afford 1.8 g of N-[3-cyano-4-(1,1-dimethylethyl)-2-thienyl]-3-methyl-2-pyrrolidinone. Yield 75%. mp=92°–94° C.

Analysis calculated for $C_{14}H_{18}N_2OS$: Theory: C, 64.09; H, 6.92; N, 10.68; Found: C, 64.35; H, 6.88; N, 10.55.

The following examples of compounds of the present invention were prepared by the general procedures outlined above.

EXAMPLE 3

N-[3-Cyano-4-(1,1-dimethylethyl)-2-pyrrolyl]-3-methyl-2-pyrrolidinone mp=167°–169° C.

Analysis calculated for $C_{14}H_{19}N_3O$: Theory: C, 68.54; H, 7.81; N, 17.13; Found: C, 68.71; H, 7.61; N, 17.10.

EXAMPLE 4

N-(3-Cyano-4-methyl-2-furyl)-3-methyl-2-pyrrolidinone mp=109°–112° C.

EXAMPLE 5

N-[3-Carbethoxy-4-(1-methylethyl)-2-thienyl]-3-methyl-2-pyrrolidinone oil

Analysis calculated for $C_{15}H_{21}NO_3S$: Theory: C, 61.02; H, 7.12; N, 4.75; Found: C, 60.73; H, 7.44; N, 4.44.

EXAMPLE 6

N-(3-Cyano-4,5-dimethyl-2-furyl)-3-methyl-2-pyrrolidinone mp=84°–86° C.

EXAMPLE 7

N-[3-Cyano-5-(1-methylethyl)-2-thienyl]-3-methyl-2-pyrrolidinone mp=83°–85° C.

Analysis calculated for $C_{13}H_{16}N_2OS$: Theory: C, 62.87; H, 6.49; N, 11.28; S, 12.91; Found: C, 63.00; H, 6.46; N, 11.14; S, 12.90.

EXAMPLE 8

N-[3-Carboxamide-4-(1,1-dimethylethyl)-2-furyl]-3-methyl-2-pyrrolidinone mp=148°–150° C.

Analysis calculated for $C_{14}H_{20}N_2O_3$: Theory: C, 63.62; H, 7.63; N, 10.63; Found: C, 63.39; H, 7.42; N, 10.39.

The following intermediates are exemplary of those intermediates contemplated by the present invention.

4-Chloro-N-[3-cyano-4-(1,1-dimethylethyl)-2-furyl]-2-methylbutanamide

4-Chloro-N-[3-cyano-4-(1,1-dimethylethyl)-2-thienyl]-2-methylbutanamide mp=115°–116° C.

4-Chloro-N-[3-cyano-4-(1,1-dimethylethyl)-2-pyrrolyl]-2-methylbutanamide

4-Chloro-N-[3-cyano-4-methyl-2-furyl]-2-methylbutanamide

4-Chloro-N-[3-carbethoxy-4-(1-methylethyl)-2-thienyl]-2-methylbutanamide oil

Analysis calculated for $C_{15}H_{22}ClNO_3S$: Theory: C, 54.29; H, 6.68; N, 4.22; Found: C, 54.13; H, 6.80; N, 3.93.

4-Chloro-N-(3-cyano-4,5-dimethyl-2-furyl)-2-methylbutanamide

4-Chloro-N-[3-cyano-5-(1-methylethyl)-2-thienyl]-2-methylbutanamide mp=100°–102° C.

Analysis calculated for $C_{13}H_{17}ClN_2OS$: Theory: C, 54.82; H, 6.02; N, 9.84; Found: C, 54.59; H, 5.76; N, 9.79.

The compounds of the present invention have been found to display both preemergent and postemergent herbicidal activity against a variety of weed species, and are therefore useful in controlling and inhibiting the growth of both broadleaf and grassy weeds in crops such as cereal grains and the like. It is therefore provided as another embodiment of the present invention a method for controlling undesired plants which comprises applying to the plants a growth inhibiting amount of a compound of the invention.

To control the growth of unwanted vegetation, the present compounds may either be applied to young plants in a growth inhibiting amount or applied to the soil prior to emergence of the plants. The compounds may be either incorporated into the soil, by using a conventional disc or harrow prior to planting the seeds of the desired crop species, or by surface applying the compounds to the soil prior to substantial plant emergence or after plant emergence. In this latter procedure the compounds are merely permitted to leach into the soil, for example with the assistance of rainfall.

The compounds of the present invention are useful in controlling a wide variety of weed species, including the following:

Barnyard Grass (*Echinochloa crus-galli*)
Common Lambsquarters (*Chenopodium album*)
Large Crabgrass (*Digitaria sanguinalis*)
Indian Mustard (*Brassica juncea*)
Redroot Pigweed (*Amaranthus retroflexus*)
Green Foxtail (*Setaria viridis*)
Wild Oat (*Avena fatua*)
Velvetleaf (*Abutilon theophrasti*)
Jimsonweed (*Datura stramonium*)
Tall Morningglory (*Ipomoea purpurea*)
Zinnia (*Zinnia elegans*)

The present compounds also display a unique selective capability in that they are safe against a wide variety of crop species, including the following:

Corn (*Zea mays*)
Cotton (*Gossypium hirsutum*)
Soybean (*Glycine max*)
Wheat (*Triticum gestivum*)
Alfalfa (*Medicago sativa*)
Sugar Beet (*Beta vulgaris*)
Rice (*Oryza sativa*)
Cucumber (*Cucumis sativus*)
Tomato (*Lycopersicon esculentum*)

The term "growth inhibiting amount", as used herein, refers to an amount of a compound of the present invention which either kills or stunts the growth of the weed species for which control is desired. This amount will generally be from about 0.10 to about 20.0 pounds of pyrrolidinone per acre (about 0.112 to about 22.4 kg/ha). The compounds are more preferably applied at rates of about 0.25 to about 8.0 pounds per acre (about 0.28 to about 8.96 kg/ha). The exact concentration of compound required varies with the weed species to be controlled, type of formulation, soil condition, climate, and related factors.

The compounds of the present invention are preferably formulated prior to use for ease of application. It is therefore provided as yet another embodiment of the present invention herbicidal compositions comprising an agriculturally-acceptable carrier together with a growth inhibiting amount of a compound of the invention. Such compositions will contain from about 0.1 to about 95.0 percent by weight of the active ingredient, depending on the composition desired. Preferred formulations will contain from about 1 to about 50 percent active ingredient. Sprayable formulations are preferred because of their ease and economy of application.

The most convenient formulations contemplated are in the form of concentrated compositions. Such formulations are diluted with water, generally at the site of application and are applied by spraying the resulting water dispersion or emulsion. The diluted compositions generally will contain the active compounds in the range from about 0.1 percent to about 10 percent by weight. Water-dispersible or emulsifiable compositions may be either solids, usually known as wettable powders, or liquids, usually known as emulsifiable concentrates or aqueous suspensions.

A typical wettable powder comprises an intimate mixture of a compound of the invention, an inert carrier, and one or more surfactants. The concentration of the active compound is usually from about 5 percent to about 90 percent by weight, ideally about 10 to about 70 percent. The inert carrier is usually chosen from among the attapulgite clays, the montmorillonite clays, the diatomaceous earths, the purified silicates, or other similar substances that are readily available. Effective surfactants, comprising from about 0.5 percent to about 10 percent by weight of the wettable powder, are chosen from among the sulfonated lignins, the condensed naphthalenesulfonates, the alkyl sulfates, and related materials.

A typical emulsifiable concentrate comprises from about 0.1 to about 6 pounds of a compound of the invention per gallon of liquid (0.012 to 0.72 kg/l.), dissolved in a mixture of an organic solvent and an emulsifier. The organic solvent is chosen with regard to its solvency and its cost. Useful solvents include the aromatics, especially the xylenes and the heavy aromatic naphthas. Hydrophilic cosolvents such as cyclohexanone and the glycol ethers such as 2-methoxyethanol may be included. Other organic solvents may also be used, including the terpenic solvents and kerosene. Suitable emulsifiers for emulsifiable concentrates are chosen from the alkylbenzenesulfonates, naphthalenesulfonates, and nonionic surfactants such as alkylphenol adducts of polyoxyethylene, and are used at similar percentages as for wettable powders.

An aqueous suspension, or flowable, is comprised of a finely ground suspension of the active ingredient dispersed in a water based system. This type of formulation is particularly useful for compounds with low water solubility. The concentration of active agent is usually from about 15 to 60 percent by weight. A typical aqueous suspension may comprise wetting and dispersing agents, antifreeze components, thickening or bulking agents as well as water and the active ingredient.

Dust compositions will contain a compound of the invention generally in an amount from about 0.1 to about 10 percent by weight. Dusts are prepared by intimately mixing and finely grinding the compound with an inert solid diluent or carrier such as ground montmorillonite clay, attapulgite clay, talc, ground volcanic rock, kaolin clay, or other inert, relatively dense substances.

Solid, granular compositions are convenient for the application of compounds of this invention to the soil. Granules comprise a compound of the invention, at a concentration of from about 0.1 to about 20 percent by weight, dispersed on a granular inert carrier, such as coarsely ground clay, of from about 0.1 to about 3 mm particle size. The compound is most conveniently applied to the clay by dissolving it in an inexpensive solvent such as acetone and applying the solution to the sized clay in an appropriate solids mixer. The solvent is then typically removed by evaporation or the like.

The formulated compounds are applied to plants and to the locus where plants are growing by conventional procedures. Sprayable compositions are easily applied by any of many types of sprayers available to the art. Self-propelled, tractor-mounted, and towed spray devices which apply the water-dispersed formulations through calibrated atomizing nozzles are available and effective. Metering applicators are also available which can apply accurately measured quantities of solid compositions to the locus to be treated. The operator of the application equipment need only take care to adjust the equipment to apply an amount of the water-dispersed or solid formulation which supplies the desired application rate of the compound, and to apply the amount uniformly to the plants to be treated.

The following are examples of typical herbicidal compositions comprehended by this invention.

| Wettable Powder | |
|---|---|
| Ingredient | Concentration by weight (%) |
| N—[3-Cyano-4-(1,1-dimethylethyl)-2-furyl]-3-methyl-2-pyrrolidinone | 50.0 |
| Igepal CA-6.30, a polyoxyethylene octyl phenol nonionic wetting agent from GAF Corp. | 20.0 |
| Barden Clay, a Kaolin clay from J. M. Huber Corp. | 30.0 |
| | 100.0 |

The active ingredient is finely divided into a powder and blended to uniformity with the agronomic carriers to form a free flowing powder that will be wetted and suspendible in water at or near the site of application to form a sprayable mixture. The composition is then sprayed on the locus where control is desired. The application is done at a volume rate so that the active ingredient is present at about 1 to about 4 pounds per acre (about 1.12 to about 4.48 kg/ha).

| Dust | |
|---|---|
| Ingredient | Concentration by weight (%) |
| N—(3-Cyano-4,5-dimethyl-2-furyl)-3-methyl-2-pyrrolidinone | 10.0 |
| Diatomite, a diatomaceous earth, Witco Chemical Corp., Inorganic Specialities Division | 90.0 |
| | 100.0 |

The pyrrolidinone is suspended in acetone and sprayed onto the diatomaceous earth carrier. The solvent is then removed by evaporation and the dry mixture is ground to a fine powder of uniform particle size of about 10 to about 40 microns. The dust formulation can be diluted at the site of application if desired by the addition of additional carrier such as silica or clay. The dust is surface applied to the soil or plants where control is desired, either by conventional ground equipment or aerially.

| Aqueous Suspension | |
|---|---|
| Ingredient | Concentration by weight (%) |
| N—[3-Carbethoxy-4-(1-methylethyl)-2-thienyl]-3-methyl-2-pyrrolidinone | 60.0 |
| Reax, lignosulfonate suspending agent, Westvaco Corp., Polychemical Dept. | 5.0 |
| Zanthum Gum thickening agent | 0.15 |
| Zeosyl 100, a precipitated hydrated silicon dioxide anticaking agent, J. M. Hubor Corp. | 1.0 |
| Antifoam C foam suppressant, Dow Corning | 0.25 |
| Water | 33.60 |
| | 100.00 |

The aqueous suspension containing the pyrrolidinone derivative is typically diluted with additional water at the site of application, and sprayed onto the locus where vegetative control is desired. The diluted aqueous suspension is applied such that the active ingredient is present at about 4 pounds per acre (4.48 kg/ha) for the effective control of unwanted vegetation such as lambsquarter, pigweed, velvetleaf and the like in crops such as corn, soybean or cereal grains.

| Ingredient | Granule Concentration by weight (%) |
|---|---|
| N—(3-Cyano-4-ethyl-2-furyl)-3-methyl-2-pyrrolidinone | 6.0 |
| Naphtha | 4.0 |
| Florex 30/60 granular clay, The Floridin Company | 90.0 |
| | 100.0 |

The herbicide is dissolved in the naphtha and then sprayed onto the dry granules under agitation. The formulated granules are sieved to provide a uniform mesh size.

The herbicidal activity of representative compounds of the present invention is illustrated by the following experiments.

EXPERIMENT 1

The initial screen used to evaluate herbicidal efficacy was conducted at a test compound concentration of 15 lbs/acre (16.8 kg/ha). In this test a standard sand:soil mixture (1:1) was sterilized and added to separate containers. Following sterilization, tomato, large crabgrass and pigweed seeds were planted in the containers by row. Each container was fertilized before treatment.

The test compounds were formulated for application by dissolving the compound into a solvent prepared by combining Toximul R and Toximul S (proprietary blends of anionic and nonionic surfactants manufactured by Stepan Chemical Company, Northfield, Ill.) into a 1:1 (v/v) mixture of acetone and ethyl alcohol. The solvent/compound solution was diluted with deionized water and applied postemergence to some planted containers and preemergence to others using a modified DeVilbiss atomizer. Postemergence treatment was made 11 to 13 days after planting while preemergence treatment was made one day after planting.

Following treatment the containers were moved to the greenhouse and watered as necessary. Observations were made 10 to 13 days after treatment using untreated control plants as standards. The degree of herbicidal activity was determined by rating the treated plants on a scale of 1 to 5. On this scale "1" indicates no injury, "2" is slight injury, "3" is moderate injury, "4" is severe injury and "5" indicates death to the plant or no seedling emergence. Also, the various types of injury of each test species were coded as follows.

A=abscission of leaves
B=burned
C=chlorosis
D=death
E=epinasty
F=formation effects
G=dark green
I=increased plant growth
L=local necrosis
N=no germination
P=purple pigmentation
R=reduced germination
S=stunting
U=unclassified injury Table I presents the herbicidal activity of typical pyrrolidinones of the present invention when evaluated in the herbicide screen described above.

TABLE I

| | Herbicide Pretest at 15 lbs/acre (16.8 kg/ha) | | | | | |
|---|---|---|---|---|---|---|
| Example No. | Preemergence | | | Postemergence | | |
| of Compound Tested | Tomato | Large Crabgrass | Pigweed | Tomato | Large Crabgrass | Pigweed |
| 1 | 1 | 4RS | 4RS | 5D | 5D | 5D |
| 2 | 1 | 1 | 1 | 1 | 1 | 1 |
| 5 | 1 | 1 | 1 | 3BS | 2BS | 1 |

EXPERIMENT 2

The herbicidal activity of some of the compounds of the present invention was further evaluated at various application rates in a multiple species greenhouse test. Several additional weed and crop species were utilized to determine the herbicidal activity and selectivity of the test compounds. Lower concentrations of the test compounds were obtained by serial dilution of the formulation described above in Experiment 1 with a mixture of the surfactant containing solvent and deionized water. The compounds were evaluated according to the 1 to 5 scale outlined above. Table II represents preemergence herbicidal test results administered at 8 lbs/acre (8.96 kg/ha) or less, while Table III represents postemergence test data administered only at 8 lbs/acre.

TABLE II

| | | Preemergence | | | | | | | | |
|---|---|---|---|---|---|---|---|---|---|---|
| Example No. of Compound Tested | Rate of Appln lbs/acre (kg/ha) | Crops | | | | | | | | |
| | | Corn | Cotton | Soybean | Wheat | Alfalfa | Sugar Beet | Rice | Cucumber | Tomato |
| 1 | 8.0 (8.96) | | | | | | | | | 2 |
| | 4.0 (4.48) | 1 | 1 | 1 | 2 | 2 | 4 | 2 | 2 | 1 |
| | 2.0 (2.24) | 1 | 1 | 1 | 1 | 1 | 1 | 1 | 1 | 1 |
| | 1.0 (1.12) | 1 | 1 | 1 | 1 | 1 | 1 | 1 | 1 | 1 |
| 2 | 8.0 (8.96) | | | | | | | | | 1 |
| 3 | 8.0 (8.96) | | | | | | | | | 1 |
| 4 | 8.0 (8.96) | | | | | | | | | 2 |
| 5 | 8.0 (8.96) | | | | | | | | | 1 |
| 6 | 8.0 (8.96) | | | | | | | | | 1 |
| 7 | 8.0 (8.96) | 1 | | | | | | | | |
| 8 | 8.0 (8.96) | | | | | | | | | 1 |

| Example No. of Compound | Rate of Appln lbs/acre | Weeds | | | | | |
|---|---|---|---|---|---|---|---|
| | | Barnyard | Lambs- | Large | | Wild | Jimson- Morning- |

TABLE II-continued

| Tested | (kg/ha) | Grass | quarter | Crabgrass | Mustard | Pigweed | Foxtail | Oat | Velvetleaf | weed | glory | Zinnia |
|---|---|---|---|---|---|---|---|---|---|---|---|---|
| 1 | 8.0 (8.96) | 2 |   | 4 | 4 | 3 | 3 | 3 | 5 |   | 5 | 4 |
|   | 4.0 (4.48) | 1 | 5 | 4 |   | 2 | 1 | 1 | 4 | 2 | 1 | 2 |
|   | 2.0 (2.24) | 1 | 4 | 2 |   | 2 | 1 | 1 | 2 | 2 | 1 | 1 |
|   | 1.0 (1.12) | 1 | 1 | 2 |   | 2 | 1 | 1 | 1 | 1 | 1 | 1 |
| 2 | 8.0 (8.96) | 1 |   | 1 | 1 | 1 | 1 | 1 | 1 |   | 1 | 1 |
| 3 | 8.0 (8.96) | 1 |   | 2 | 1 | 1 | 2 | 1 | 1 |   | 1 | 1 |
| 4 | 8.0 (8.96) | 1 |   | 2 | 1 | 1 | 2 | 1 | 1 |   | 1 | 2 |
| 5 | 8.0 (8.96) | 1 |   | 2 | 1 | 1 | 1 | 1 | 2 |   | 1 | 1 |
| 6 | 8.0 (8.96) | 1 |   | 1 | 1 | 1 | 1 | 1 | 1 |   | 1 | 1 |
| 7 | 8.0 (8.96) |   |   | 1 |   | 1 | 1 |   | 1 |   | 1 | 1 |
| 8 | 8.0 (8.96) | 2 |   | 2 | 1 | 1 | 3 | 2 | 2 |   | 2 | 2 |

TABLE III

| Example No. of Compound Tested | Rate of Appln lbs/acre (kg/ha) | Corn | Tomato | Large Crab-grass | Postemergence Pigweed | Foxtail | Velvet-leaf | Morning-glory | Zinnia | Barnyard Grass | Mustard | Wild Oat |
|---|---|---|---|---|---|---|---|---|---|---|---|---|
| 1 | 8.0 (8.96) |   | 4 | 5 | 5 | 3 | 5 | 4 | 5 | 3 | 5 | 4 |
| 2 | 8.0 (8.96) |   | 1 | 1 | 1 | 1 | 1 | 1 | 2 | 1 | 1 | 1 |
| 3 | 8.0 (8.96) |   | 1 | 1 | 1 | 1 | 1 | 1 | 1 | 1 | 1 | 1 |
| 4 | 8.0 (8.96) |   | 1 | 2 | 2 | 1 | 1 | 1 | 1 | 1 | 2 | 1 |
| 5 | 8.0 (8.96) |   | 1 | 2 | 2 | 2 | 1 | 2 | 2 | 2 | 2 | 2 |
| 6 | 8.0 (8.96) |   | 2 | 1 | 1 | 2 | 2 | 2 | 3 | 1 | 3 | 1 |
| 7 | 8.0 (8.96) | 1 |   | 1 | 1 | 1 | 2 | 1 | 1 |   |   |   |
| 8 | 8.0 (8.96) |   | 2 |   | 3 | 1 | 1 | 1 | 1 | 3 | 2 | 1 |

The compounds of the present invention may also be used in combination with one or more herbicides. It is therefore provided as another embodiment of the present invention a herbicidal combination comprising a present compound together with one or more herbicides. These combinations are preferred when a broader spectrum of weed control is desired than either herbicide can provide when used alone. For example, the present compounds are particularly effective against broadleaf weeds, and therefore when combined with one or more grass herbicides, an extremly useful and effective herbicidal combination is provided. Preferred grass herbicides to be employed in these combinations include the dinitroanilines, such as trifluralin, benefin, butralin, chlornidine, dinitramine, ethalfluralin, fluchloralin, isopropalin, nitralin, oryzalin, pendimethalin, prodiamine, profluralin, prosulfalin, and the like. A preferred combination of the present invention comprises trifluralin and N-[3-cyano-4-(1,1-dimethylethyl)-2-furyl]-3-methyl-2-pyrrolidinone. Other herbicides which may be used in combination with a presently disclosed active agent include alachlor, ametryn, amitrole, atrazine, bentazon, bifenox, butachlor, butam, buthidazole, butylate, chloramben, chlorbromuron, cyanazine, dichlorprop, diuron, dinoseb, EPTC, fenac, fluometuron, linuron, methazole, metolachlor, metribuzin, nitrofen, norflurazon, pebulate, perfluidone, prometon, prometryn, propachlor, simazine, tebuthiuron, terbutryn, triallate, triclopyr, propanil, vernolate and the like.

Also provided by this invention is a method for controlling undesired plants which comprises applying to the plants a growth inhibiting amount of a combination of a present compound together with one or more herbicides. The application rate desired for each of the individual herbicides in the combination is dependent on a number of factors, including the type of weeds to be controlled, the herbicides that will be used in the combination, climate and soil conditions, the weed population and related factors. Generally, the present compounds will be employed in combination with other herbicides in a ratio of about one to about ten parts by weight of pyrrolidinone and about ten to about one part by weight of another herbicide. More preferable ratios of active ingredients will be from about one to about five parts by weight of a present compound and about five to about one part by weight of another herbicide. A particularly preferred combination will contain the component herbicides in a weight ratio of about one to one. The combinations will be applied at rates which are effective to control the undesired plants to the desired degree.

The combinations provided herein are formulated in the identical manner which was described for the present novel compounds alone, and at similar concentrations. The active components of the combination may be combined as technical materials and later formulated as a whole, or formulated individually and applied either as a combination or individually to the locus of the undesired plants.

The following is an example of a typical herbicidal composition containing a combination of the invention.

| Tank-Mix Composition | |
|---|---|
| Ingredient | Concentration by weight (%) |
| N—[3-Cyano-4-(1,1-dimethylethyl)-2-furyl]-3-methyl-2-pyrrolidinone formulated as a 50% wettable powder | 65.0 |
| Trifluralin formulated as an emulsifiable concentrate at 4 lbs/gallon (0.48 kg/l.) | 35.0 |
|  | 100.0 |

The wettable powder formulation is added to an aqueous solution of the emulsifiable concentrate under agitation in a suitable spray applicator. The mixture is sprayed on the soil surface and then typically incorporated into the soil at a depth of about 3 to 4 inches prior to planting.

We claim:

1. A compound of the formula

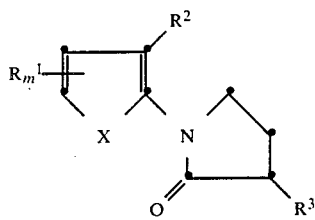

wherein:
$R^1$ is $C_1$–$C_{10}$ alkyl or $C_3$–$C_8$ cycloalkyl;
$R^2$ is cyano or

$R^3$ is $C_1$–$C_6$ alkyl;
$R^4$ is hydroxy, $C_1$–$C_6$ alkoxy or $NH_2$;
m is 1 or 2; and
X is O, S or NH.

2. A compound of claim 1 wherein $R^3$ is methyl.
3. A compound of claim 2 wherein $R^2$ is cyano.
4. A compound of claim 3 wherein X is oxygen.
5. A compound of claim 4 wherein m is two.
6. The compound of claim 5 which is N-(3-cyano-4,5-dimethyl-2-furyl)-3-methyl-2-pyrrolidinone.
7. A compound of claim 4 wherein m is one.
8. The compound of claim 7 which is N-[3-cyano-4-(1,1-dimethylethyl)-2-furyl]-3-mSethyl-2-pyrrolidinone.
9. A compound of claim 2 wherein $R^2$ is carbethoxy.
10. A compound of claim 9 wherein X is sulfur.
11. A compound of claim 10 wherein m is one.
12. The compound of claim 11 which is N-[3-carbethoxy-4-(1-methylethyl)-2-thienyl]-3-methyl-2-pyrrolidinone.
13. A method for controlling undesired plants which comprises applying to the plants a growth inhibiting amount of a compound of claim 1.
14. The method of claim 13 wherein the compound is N-(3-cyano-4,5-dimethyl-2-furyl)-3-methyl-2-pyrrolidinone.
15. The method of claim 13 wherein the compound is N-[3-cyano-4-(1,1-dimethylethyl)-2-furyl]-3-methyl-2-pyrrolidinone.
16. The method of claim 13 wherein the compound is N-[3-carbethoxy-4-(1-methylethyl)-2-thienyl]-3-methyl-2-pyrrolidinone.
17. A herbicidal composition which comprises a growth inhibiting amount of a compound of claim 1 and an agriculturally-acceptable carrier.
18. The composition of claim 17 wherein the compound is N-(3-cyano-4,5-dimethyl-2-furyl)-3-methyl-2-pyrrolidinone.
19. The composition of claim 17 wherein the compound is N-[3-cyano-4-(1,1-dimethylethyl)-2-furyl]-3-3-methyl-2-pyrrolidinone.
20. The composition of claim 13 wherein the compound is N-[3-carbethoxy-4-(1-methylethyl)-2-thienyl]-3-methyl-2-pyrrolidinone.

* * * * *